United States Patent [19]

Davis

[11] Patent Number: 5,406,012
[45] Date of Patent: * Apr. 11, 1995

[54] HETEROCATALYST SYSTEM

[75] Inventor: Mark E. Davis, Blacksburg, Va.

[73] Assignee: The Dow Chemical Company, Midland, Mich.

[ * ] Notice: The portion of the term of this patent subsequent to Dec. 20, 2011 has been disclaimed.

[21] Appl. No.: 355,518

[22] Filed: May 23, 1989

[51] Int. Cl.$^6$ .................. C07C 5/03; B01J 27/18; B01J 29/02

[52] U.S. Cl. ................... 585/277; 585/275; 502/208; 502/213; 502/214; 423/305; 423/306

[58] Field of Search ................ 423/306, 305, 326; 502/208–213; 208/46, 111, 134; 585/275, 277

[56] References Cited

FOREIGN PATENT DOCUMENTS 0146389 6/1985 European Pat. Off. .

Primary Examiner—Anthony McFarlane
Attorney, Agent, or Firm—Barbara J. Tribble

[57] ABSTRACT

A composition comprising a crystalline aluminumphosphate material having a three-dimensional microporous crystal framework structure whose chemical composition expressed in terms of mole ratios of oxides is $$Al_2O_3: 1.0\pm0.2\ P_2O_5;$$

and which is further defined as having an x-ray powder diffraction pattern characterized by d spacings at less than about 40 degrees two-theta as measured using copper K-alpha radiation that are substantially as shown in the Table and a metal in an amount of up to about 25 percent by weight is disclosed. The composition can be prepared by impregnating the crystalline aluminumphosphate material with the metal in an amount of up to about 25 percent by weight. The resultant heterocatalyst system can be used to shape-selectively hydrogenate an unsaturated organic compound, such as, for example an olefin, aldehyde or ketone.

9 Claims, 1 Drawing Sheet

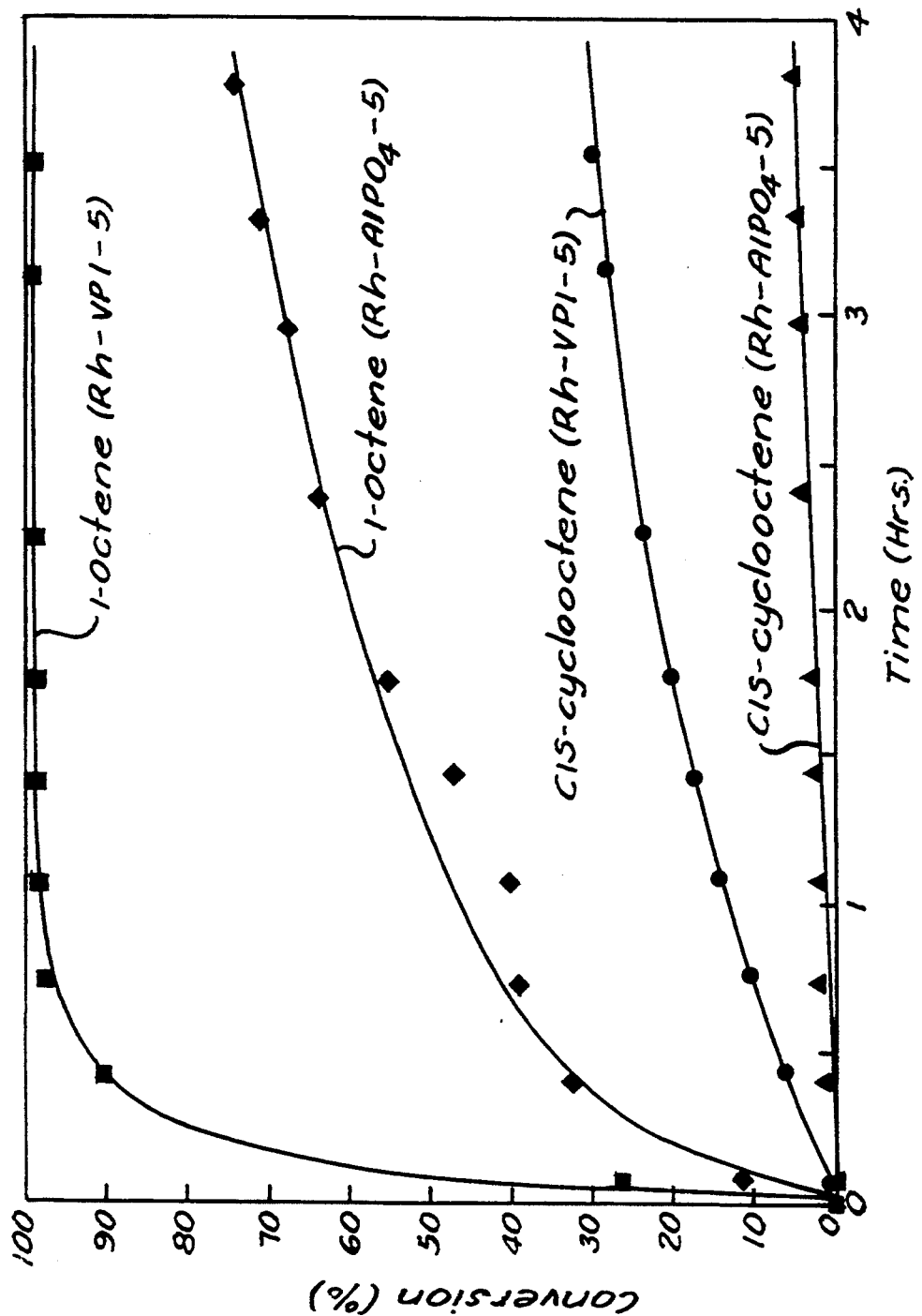

HETEROCATALYST SYSTEM

BACKGROUND OF THE INVENTION

This invention relates to the field of catalysis. More specifically, the invention relates to a heterocatalyst system wherein the catalytic results stems from two catalyst types, a metal part and the metal combined with another catalytically active or inactive substance.

In the use of zeolites as molecular sieves and catalyst supports, a great effort has been made to improve the activity and selectivity of these catalysts by devising a heterocatalyst system with a zeolite acting as a catalyst and a metal deposited on or reacted in the formation of the zeolite, thus due to its molecular sieve function further enhancing the catalytic activity of the zeolite.

One example of such a heterocatalyst system is described in U.S. Pat. No. 4,444,898, wherein a metal complex is reacted with a hydroxyl group that is in a zeolite or molecular sieve pore, and used for carbonylation and hydrogenation catalysis. Among these systems are the rhodium reaction product with a hydroxyl group within a Type 13X or 13Y zeolite cage. U.S. Pat. No. 4,622,308 describes a catalyst for the production of hydrocarbons from the synthesis gas which comprises an iron-containing Fischer-Tropsch catalyst, a zeolite and at least one metal consisting from the group ruthenium, rhodium, platinum, palladium, iridium, cobalt and molybdenum. The zeolites used are preferably X zeolites, Y zeolite, and mordenite. The metal is present in amounts from 5 to 80 percent by weight, based on the combined weight of the iron oxide and zeolite. U.S. Pat. No. 4,623,632 describes a catalytic composite for the conversion of hydrocarbons comprising a non-acidic zeolite having deposited thereon catalytically effective amounts of a Group VIII metal component and a sufficient surface-deposited alkali metal to provide a surface-deposited alkali metal index of at least 10. Typical of the non-acidic zeolites are X zeolite, Y zeolite, L zeolite, and mordenite. U.S. Pat. No. 3,376,215 discloses a hydrocarbon conversion catalyst comprising a cocatalytic solid support containing a Group VIII metal, the support comprising (1) an adsorbant refractory inorganic oxide and (2) a mordenite zeolite. The mordenite zeolite has deposited thereon a metal selected from the class of alkali metals, alkaline earth metals and mixtures thereof.

European Patent Application 185,329 discloses dewaxing catalysts and a process employing silicoaluminumphosphate molecular sieves. The catalysts comprise at least (1) a silicoaluminumphosphate molecular sieve, and (2) optionally, and in the instance of hydrodewaxing, at least one hydrogenation component. The silicoaluminumphosphate molecular sieves are disclosed in U.S. Pat. No. 4,440,871. A general paper discussing heterocatalysts is the article by D. C. Bailey et al., entitled "Immobilized Transition-Metal Carbonyls and Related Catalysts," *Chem. Rev.* 81(2), 109–145 (1981).

Thus it can be seen in the prior art that it is known to combine metals with zeolites in order to produce heterocatalysts. U.S. Pat. No. 4,444,898, cited supra, discloses using such a heterocatalyst system for hydrogenation. However, it is also known in the art that zeolites X, L, Y and mordenite, as well as aluminumphosphate and silicoaluminumphosphate molecular sieves in general, have pore sizes less than or equal to about 9 Angstroms. Thus, their use for performing a catalytic shape-selective hydrogenation of a given selected molecule is limited by the pore size. In view of this, it would be desirable in the art to have a heterocatalyst system allowing for shape-selective hydrogenation of molecules having a diameter greater than about 9 angstroms.

SUMMARY OF THE INVENTION

Accordingly, the present invention provides a heterocatalyst system, a means to prepare it and a process for using it for hydrogenation that can be applied to the shape-selective hydrogenation of molecules larger than 9 angstroms. This is because the molecular sieve that forms an integral part of the heterocatalyst system itself has pores of a kinetic diameter larger than about 9 angstroms, and in fact, from about 3 to about 14 angstroms.

The present invention is a composition comprising a crystalline aluminumphosphate material having a three-dimensional microporous crystal framework structure whose chemical composition expressed in terms of mole ratios of oxides is

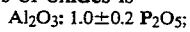

Al$_2$O$_3$: 1.0±0.2 P$_2$O$_5$;

and which is further defined as having an x-ray powder diffraction pattern characterized by d-spacings at less than about 40 degrees two-theta as measured using copper K-alpha radiation that are substantially as shown in the Table, and a metal in an amount of up to about 25 percent by weight.

The present invention also provides a method of preparing the composition comprising impregnating the crystalline aluminumphosphate material with a metal.

Finally, the present invention comprises a method of using the heterocatalyst composition to perform a catalytic hydrogenation of an unsaturated organic compound comprising reacting the composition with the unsaturated organic compound.

BRIEF DESCRIPTION OF THE DRAWING

The figure shows a comparison of the conversion rates, plotted as percent conversion over timer of 1-octene and cis-cyclooctene when each is exposed to the heterocatalyst system of the present invention and to a rhodium complex of the known zeolite AlPO$_4$-5.

DESCRIPTION OF THE PREFERRED EMBODIMENTS

The compositions of the present invention are a combination of the crystalline aluminumphosphate material and a selected metal. The crystalline aluminumphosphate compositions are described in detail in copending U.S. application Ser. No. 207,850, filed Jun. 15, 1988, which is a Continuation-in-Part of U.S. application Ser. No. 090,801, filed Aug. 28, 1987, now abandoned. These applications describe and claim the crystalline aluminumphosphate materials themselves and are incorporated by reference herein. The Table below shows the X-ray powder diffraction data for the aluminumphosphate materials described in the application and used in preparing the heterocatalyst system of the present inventions. These aluminumphosphate materials have been designated by the letters "VPI-5."

TABLE

X-Ray Powder Diffraction Data for the Crystalline Aluminumphosphate Material, designated "VPI-5"

| Two-theta (degrees) | d(Å) | $I/I_o$ (%) |
| --- | --- | --- |
| 5.36 | 16.48 | vs |
| 9.32 | 9.49 | w |
| 10.75 | 8.23 | m |
| 14.35 | 6.17 | m |
| 16.16 | 5.48 | w |
| 18.68 | 4.75 | m |
| 21.66 | 4.10 | m |
| 21.92 | 4.05 | m |
| 22.39 | 3.97 | m |
| 22.56 | 3.94 | m |
| 23.59 | 3.77 | m |
| 24.46 | 3.64 | w |
| 26.12 | 3.41 | w |
| 27.17 | 3.28 | m |
| 28.19 | 3.17 | w |
| 28.96 | 3.08 | w |
| 29.48 | 3.03 | w |
| 30.28 | 2.95 | w |
| 30.88 | 2.90 | w |
| 32.71 | 2.74 | m |
| 34.05 | 2.63 | w |
| 35.86 | 2.50 | w |
| 38.32 | 2.35 | w |

The aluminumphosphate materials used in the present invention are described as having an x-ray diffraction pattern characterized by d-spacings at less than 40 degrees two-theta as measured using copper K-alpha radiation that are substantially as shown in the Table. "Substantially" as used herein means that the d spacings given in the Table are within the allowance for experimental error, and thus allow for differences attributable to variances in equipment and technique. The Table shows the characteristic d-spacings of VPI-5 between about three degrees two-theta and about 40 degrees two-theta as measured using copper K-alpha radiation. "Characteristic" and "characterizing" as used herein refer to those d spacings representing all peaks having intensitites relative to the largest peak greater than or equal to about 10. These peaks are shown as having intensities described as "vs" for very strong or "m" for medium. Peaks of lesser intensity, described as having weak ("w") intensities, are thus excluded from this definition. The d spacings remain substantially the same after VPI-5 samples are heated, although the intensities may change. The experimental X-ray diffraction patterns shown in the Table were obtained in an automated powder diffraction unit using copper K-alpha radiation.

In the present invention the described crystalline aluminumphosphate materials are combined preferably with any metal, more preferably with a Group A metal and still more preferably with a metal selected from the group consisting of iron, gold, platinum, palladium, nickel, rhodium and mixtures thereof. Still more preferred among these are platinum, palladium, nickel, rhodium and mixtures of thereof. The metal is present in the composition in an amount up to about 25 percent by weighty and more preferred is an amount up to about 5 percent by weight. The metal is not incorporated, in gross, in the zeolite structure during the zeolite structure forming process, thus forming a reaction product, but rather is combined with the molecular sieve in an exchange or adsorption.

In order to prepare the compositions of the present invention it is preferred to impregnate the crystalline aluminumphosphate material with the desired metal. For this purpose, it is preferred to begin with a metal-containing complex. Preferred metal-containing complexes include, for example, metal carbonyls, metal acetates, metal acetyl acetonates, metal nitrates, metal carbonates and mixtures thereof. While the oxidation state of the metal in the metal-containing complex initially can vary, it is desirable to achieve a metal oxidation state of zero concurrent with or after impregnation. Thus, in order to achieve complete reduction of the metal-containing complex to the metal, exposure to hydrogen is optionally desirable, either during impregnation or immediately following impregnation.

It is desirable to perform the impregnation by dissolving the metal-containing complex in a solvent. For example, water, acetone, or other commonly used solvents can be employed. Following dissolution of the metal-containing compound, the solution is slurried with the crystalline aluminumphosphate material. Slurrying together for several hours is preferred in order to effect the impregnation. Following this, the solvent can be removed by means known to those skilled in the art, such as evacuation.

The result of the impregnation is a solid composition of the present invention. This composition has a wide variety of potential uses, such as for hydrogenation.

In order to use this composition for a catalytic shape-selective hydrogenation of an unsaturated organic compound, such as an olefin aldehyde, or ketone, it is desirable to react it with the unsaturated compound. However, in order to obtain shape-selective behavior, it is desirable to also "poison" any metal that may have been adsorbed onto the surface of the aluminumphosphate material. The "poisoning" of the metal on the surface allows for catalytic action of the metal adsorbed in the pores of the aluminumphosphate composition, and thus helps to ensure catalysis of the subject compound without undesired catalysis of other compounds, i.e., the catalysis therefore is shape-selective. For this poisoning, phosphine, such as triorthotoluophosphine, is preferred, and mercaptans can also be used. Other agents suitable for poisoning known to those skilled in the art may be selected, with the proviso that the poisoning agent should have sufficiently large a kinetic diameter to not be adsorbed in the micropores of the composition. The poisoning of the composition is preferably effected by exposing the composition to the poisoning agent, concurrently with the reaction step. A molar excess of phosphine is desired. Confirmation of the poisoning of surface metal can be done by contacting the composition with a reacting molecule that has a kinetic diameter too large to be adsorbed in the micropores, to observe whether reaction products are produced over a period of several hours.

The reaction step, which is generally done in a slurry phase reaction, is preferably rapid and complete. The fact that 1-octene and cis-cyclooctene can be hydrogenated using a composition of the present invention based upon the crystalline aluminumphosphate material as described, particularly in its poisoned form, is attributable in part to the pore size of that material.

The following example is given to more fully illustrate the present invention, and is not intended to bey nor should it be construed as being, indicative of the scope of the invention. All parts and percentages are by weight unless otherwise indicated.

EXAMPLE

The crystalline aluminumphosphate material described in U.S. application Ser. No. 207,850, filed Jun. 15, 1988, and prepared according to Example 1 of that application, is impregnated with rhodium by the following procedure. About 20 mg of the complex rhodium acetyl acetonate is slurried in 20 cc of acetone. About 0.8 g of the aluminumphosphate VPI-5 material is then added to the rhodium acetyl acetonate/acetone slurry and the slurried maintained overnight. The acetone is removed by evacuation. The resulting composition of the present invention is found to contain approximately 1 weight percent rhodium. The composition is exposed to hydrogen at 1 atmosphere and 30° C. The black color is understood to indicate the presence of rhodium metal.

Approximately 0.1 g of the composition is slurried in 20 cc of a reactant solution comprising 2 weight percent of 1-octene and 2 weight percent of cyclooctene in a decane solvent. This mixture is blanketed with hydrogen fixed at 1 atmosphere pressure. At the same time a 50 molar excess, compared to rhodium, of triorthotoluophosphine is also added.

The results of hydrogenating 1-octene and cis-cyclooctene with the composition of the present invention is shown in the Figure. The Figure also includes comparative data as discussed in the Comparative Example below. Thus, the conversion of large molecules, notably the cis-cyclooctene, not readily reacted in other molecular sieves containing twelve T-atom rings or less is demonstrated by the hydrogenation of cis-cyclooctene using the composition of the present invention.

COMPARATIVE EXAMPLE 1

A rhodium-containing complex of the known zeolite AlPO$_4$-5, as described in U.S. Pat. No. 3,414,602, is also prepared using essentially identical impregnation procedures as are described in the Example above. Exposure to hydrogen and poisoning are also performed. In order to confirm the poisoning of the surface rhodium, the rhodium-AlPO$_4$-5 complex is contacted with dimethylcyclooctene and decane at 30° C. and 1 atmosphere hydrogen with a 50 molar excess of triorthotoluophosphine added. No reaction products are produced over a period of 12 hours. The complex is then slurried with the reactant materials as described in the Example above. A comparison of the results of hydrogenating 1-octene and cis-cyclooctene with the rhodium complex of AlPO$_4$-5, designated Rh-AlPO$_4$-5, and the rhodium complex of the present invention, designated Rh-VPI-5, are given in the Figure. The Figure shows that the 1-octene and cis-cyclooctene are readily hydrogenated by the composition of the present invention, but that the conversion rate for cis-cyclooctene using the Rh-AlPO$_4$-5 is much slower, with only very insignificant conversion during the first hour.

What is claimed is:

1. A heterocatalyst composition comprising
  (1) a crystalline material having a three-dimensional microporous crystal framework structure whose chemical composition expressed in terms of mole ratios of oxides includes $Al_2O_3$: 1.0+0.2 $P_2O_5$;

and, optionally, from about 0.001 to about 3 moles of at least one oxide of silicon, magnesium, titanium, cobalt, tin and zirconium, per mole of $Al_2O_3$, and which is further defined as having an x-ray powder diffraction pattern characterized by d spacings at less than about 40 degrees two-theta as measured using copper K-alpha radiation that are substantially as shown in the Table, and (2) a metal, adsorbed or exchanged into or onto the crystalline material, in an amount of up to about 25 percent by weight.

2. The composition of claim 1 wherein the metal is selected from the group consisting of iron, silver, gold, platinum, palladium, nickel, rhodium and mixtures thereof.

3. The composition of claim 2 wherein the metal is selected from the group consisting of platinum, palladium, nickel, rhodium and mixtures thereof.

4. The composition of claim 1 wherein the metal is in amount up to about 5 percent by weight.

5. A process for hydrogenating an unsaturated organic compound comprising reacting an unsaturated organic compound with a heterocatalyst composition of a crystalline material having a three-dimensional microporous crystal framework structure whose chemical composition expressed in terms of mole ratios of oxides includes $Al_2O_3$: 1.0+0.2$P_2O_5$;

and, optionally, from about 0.001 to about 3 moles of at least one oxide Of silicon, magnesium, titanium, cobalt, tin and zirconium, per mole of $Al_2O_3$, and which is further defined as having an x-ray powder diffraction pattern characterized by d spacings at less than about 40 degrees two-theta as measured using copper K-alpha radiation that are substantially as shown in the Table, said crystalline material having a metal in an amount of up to about 25 percent by weight adsorbed or exchanged therewith.

6. The process of claim 5 wherein the unsaturated organic compound is selected from the group consisting of olefins, aldehydes, ketones and mixtures thereof.

7. The process of claim 6 wherein the unsaturated organic compound is an olefin.

8. The process of claim 5 wherein the metal is selected from the group consisting of iron, silver, gold, platinum, palladium, nickel, rhodium and mixtures thereof.

9. The process of claim 8 wherein the metal is selected from the group consisting of platinum, palladium, nickel, rhodium and mixtures thereof.

* * * * *